(12) United States Patent
Krinninger et al.

(10) Patent No.: US 11,517,182 B2
(45) Date of Patent: Dec. 6, 2022

(54) PASSIVE SURGICAL MANIPULATOR HAVING A HANDHELD DRIVE UNIT

(71) Applicant: Brainlab Robotics GmbH, Munich (DE)

(72) Inventors: Maximilian Krinninger, Weßling-Oberpfaffenhofen (DE); Stephan Nowatschin, Munich (DE)

(73) Assignee: Brainlab Robotics GmbH, Munich (DE)

( * ) Notice: Subject to any disclaimer, the term of this patent is extended or adjusted under 35 U.S.C. 154(b) by 345 days.

(21) Appl. No.: 16/615,799

(22) PCT Filed: May 14, 2018

(86) PCT No.: PCT/EP2018/062331
§ 371 (c)(1),
(2) Date: Nov. 21, 2019

(87) PCT Pub. No.: WO2018/215226
PCT Pub. Date: Nov. 29, 2018

(65) Prior Publication Data
US 2020/0170488 A1    Jun. 4, 2020

(30) Foreign Application Priority Data

May 23, 2017    (DE) .......................... 102017111289.8

(51) Int. Cl.
*A61B 1/00*        (2006.01)
*A61B 34/00*      (2016.01)
(Continued)

(52) U.S. Cl.
CPC .......... *A61B 1/00149* (2013.01); *A61B 34/74* (2016.02); *A61B 90/06* (2016.02); *B25J 9/10* (2013.01); *A61B 2090/064* (2016.02)

(58) Field of Classification Search
CPC ........... A61B 1/00; A61B 90/00; A61B 90/06; A61B 34/00; A61B 34/74; B25J 9/10
See application file for complete search history.

(56) References Cited

U.S. PATENT DOCUMENTS 6,368,332 B1    4/2002    Salcudean et al.

FOREIGN PATENT DOCUMENTS

DE    10 2013 209 122 A1    11/2014
DE    10 2014 016 823 A1    5/2016
(Continued)

OTHER PUBLICATIONS

Office Action issued in corresponding Korean Patent Application No. 10-2019-7037878 dated Sep. 13, 2022.

*Primary Examiner* — Christopher J Beccia
(74) *Attorney, Agent, or Firm* — Blank Rome LLP

(57) ABSTRACT

A passive surgical manipulator for holding and positioning a surgical instrument is described. The passive surgical manipulator has a frame, a first suspension arm arrangement connecting the frame in an articulated manner to a first joint, and a second suspension arm arrangement connecting the frame in an articulated manner to a second joint. The two suspension arm arrangements are implemented so that the first joint is displaceable in a first motion plane and the second joint is displaceable in a second motion plane. Also, a first actuating device has a first interface, a second actuating device has a second interface, a third actuating device has a third interface, and a fourth actuating device has a fourth interface for temporarily receiving a corresponding interface of a handheld drive unit for transferring an actuating motion to displace the first and second joints.

22 Claims, 8 Drawing Sheets

(51) Int. Cl.
*A61B 90/00* (2016.01)
*B25J 9/10* (2006.01)

(56) References Cited

FOREIGN PATENT DOCUMENTS

| | | |
|---|---|---|
| DE | 10 2014 016 824 A1 | 5/2016 |
| DE | 10 2015 104 810 A1 | 9/2016 |
| DE | 10 2015 104 819 | 1/2018 |
| EP | 1 658 016 A1 | 5/2006 |
| EP | 3 130 305 A1 | 2/2017 |
| WO | 01/34017 A2 | 5/2001 |
| WO | 2005/030074 A1 | 4/2005 |
| WO | 2014/198784 A1 | 12/2014 |
| WO | 2016/209769 A1 | 12/2016 |

PASSIVE SURGICAL MANIPULATOR HAVING A HANDHELD DRIVE UNIT

CROSS-REFERENCE TO RELATED APPLICATIONS

This application is a National Stage of International Patent App. No. PCT/EP2018/062331, filed on May 14, 2018, which claims priority to German Patent App. No. DE 10-2017-111-289.8, filed on May 23, 2017, the disclosures of which are incorporated by reference in their entirety.

FIELD OF THE INVENTION

The invention relates to a passive surgical manipulator for holding and positioning a surgical instrument, having a frame, a first suspension arm arrangement comprising at least one suspension arm and connecting the frame in an articulated manner to a first joint associated with the instrument, and a second suspension arm arrangement comprising at least one suspension arm and connecting the frame in an articulated manner to a second joint associated with the instrument, the two suspension arm arrangements being implemented so that the first joint is displaceable in a first motion plane and the second joint is displaceable in a second motion plane, the first suspension arm arrangement being connected to the frame at first and second actuating devices and the second suspension arm arrangement being connected to the frame at third and fourth actuating devices.

The invention further relates to a hand-held drive unit for using with a passive surgical manipulator of the type described above. The invention further relates to a surgical system comprising at least one manipulator of the type described above and a drive unit of the type described above. The invention further relates to a method for setting a specified position of two joints of a passive surgical manipulator of the type described above.

BACKGROUND

Such a surgical manipulator device is known from EP 1 658 016 B1, for example. The device disclosed there is provided for holding an endoscope and is fundamentally designed without a motor. The device comprises a frame having a suspension arm arrangement comprising at least two suspension arms and connecting the frame in an articulated manner to a first joint associated with the instrument, and having a second suspension arm arrangement comprising at least two suspension arms and connecting the frame in an articulated manner to a second joint associated with the first instrument, the suspension arms of the first suspension arm arrangement being pivotably supported relative to each other and relative to the frame about pivot axes, and the pivot axes running parallel to each other, and the two suspension arm arrangements being implemented so that the first joint is displaceable in a first motion plane and the second joint is displaceable in a second motion plane, the first motion plane being displaceable relative to the second motion plane. Said arrangement is used in EP 1 658 016 for compensating for a changing distance of the first and second joints for different pivoting or displacing of the first and second suspension arm arrangements. This is necessary particularly because the instrument is directly connected to the joints. It is particularly disadvantageous for such a device that it is difficult to connect the frame to a stand, because the frame must also allow the displacement of the plane.

The surgical manipulator device of the present invention is particularly intended for mounting on a mounting arm, as described in DE 10 2014 016 823 A1, DE 10 2014 016 824 A1, DE 10 2015 104 810 A1, DE 10 2015 104 819 A1, and EP 3 130 305 A1. The disclosed contents thereof with respect to the mounting arm described therein is incorporated herein in their entirety.

SUMMARY OF THE INVENTION

The object of the present invention is to disclose a simple manipulator device, a handheld drive unit, a system, and a method, by means of which simple positioning of a surgical instrument is possible.

The object is achieved according to the invention for a passive surgical manipulator of the type described above, in that the first actuating device comprises a first interface, the second actuating device comprises a second interface, the third actuating device comprises a third interface, and the fourth actuating device comprises a fourth interface for temporarily receiving a corresponding interface of a handheld drive unit, so that the handheld drive unit can be coupled temporarily and sequentially to the first, second, third, and fourth interfaces for transferring an actuating motion, in order to displace the first and second joints and position the same in a predetermined specified position.

A surgical manipulator is thus produced having no drive unit itself and thus being simple in construction and inexpensive to manufacture. It is possible, rather, that the entire driving takes place by means of a single drive unit, namely the handheld drive unit for coupling temporarily and sequentially to the first, second, third, and fourth interfaces. Thus only one single drive motor, mounted in the handheld drive unit, is necessary for setting the first and second suspension arm arrangements.

The first and second suspension arm arrangements are preferably self-blocking in design. It is thereby achieved that even after the handheld drive unit is removed, the position of the suspension arm arrangement is retained.

In a further preferred embodiment, the surgical manipulator comprises a mounting segment for mounting the manipulator on a surgical mounting arm. The surgical mounting arm is particularly implemented as a robotic mounting arm or stand and is preferably implemented as disclosed in DE 10 2014 016 824 A1, DE 10 2014 016 823 A1, and DE 10 2015 104 819 A1. The disclosed contents of said publications are incorporated herein in their entirety relating to the mounting arm.

In a further preferred embodiment of the invention, it is provided that the interfaces by means of which the handheld drive unit can be coupled temporarily and sequentially are spatially separated from each other. Intuitive operation of the surgical manipulator is thereby possible and the operator can see by implication, due to the design of the kinematics, which of the interfaces he must couple the drive unit to in order to set the first and second suspension arm arrangements.

In a further preferred embodiment, the interfaces are implemented at a common coupling cutout. Four different segments are then preferably implemented in said coupling cutout and form four interfaces. Said interfaces can be disposed supported axially one behind the other, for example. For example, it is conceivable that every interface is formed by an output drive disc comprising a central through hole, so that when the handheld drive unit is applied, said unit makes contact with all four output drive discs and can drive each separately. In this manner, operation is further simplified, because a user need not apply the handheld drive unit at different positions of the manipulator, but rather only at the common coupling cutout.

It is thereby preferable that the interfaces are implemented for positively receiving the handheld drive unit and for positively transmitting the actuating motion. By positively receiving the drive unit, a defined position of the drive unit relative to the interfaces is achieved. Positively transmitting the actuating motion results in a defined actuating motion transmission with no slipping.

Alternatively, the interfaces are implemented for positively receiving the handheld drive unit and for transmitting the actuating motion by means of a force fit. Each interface according to the present embodiment particularly comprises a ferromagnetic coupling element. That is, an output drive segment of the handheld drive unit and a corresponding coupling element of the interface are coupled by means of magnetic force. An advantage thereby is that when coupling, no determined position needs to be assumed, but rather, for example, every type rotational orientation can be coupled without partitioning. Furthermore, smooth surfaces can thus be provided as preferred for hygienic reasons in the surgical area.

The surgical manipulator preferably comprises at least one sensor for determining a force acting on the first and/or the second joint. It is thereby possible to determine a force acting on a received instrument. This can be used, for example, for determining whether a patient has been incorrectly stressed for a motion of the first and second suspension arm arrangement. It is conceivable, for example, that a user makes an operating error and sets the suspension arm arrangement in an unnecessary manner. In this case, by determining the force at the joints, feedback can be given warning the user of the manipulator. Safety is thereby particularly improved.

According to a further preferred embodiment, the manipulator comprises a control unit having a processor and software means implemented for determining an actuating motion required at each interface for reaching the specified setting, based on a predetermined specified setting for the first and second joints. A pose of the first and second suspension arm arrangements is preferably thereby determined. The control unit is particularly preferably set up for providing signals representing the determined actuating motions at the handheld drive unit or a peripheral device. Alternatively, the handheld drive unit itself is able to determine an actuating motion required at each interface for reaching the specified setting, based on a predetermined specified setting for the first and second joints. If this is achieved by the control unit of the manipulator, the signals representing the determined actuating motions are preferably sent to the handheld drive or a peripheral device. This can be done wirelessly, for example. A peripheral device can be particularly a mounting arm on which the manipulator is received, or a surgical navigation system. It is conceivable, for example, that a surgical navigation system sends a predetermined specified setting to the manipulator, the manipulator determines the corresponding actuating motions based on the received predetermined specified setting, said motions are then transmitted to the handheld drive unit, and the handheld drive unit then performs the actuating motions when coupled to the corresponding interface.

Each interface preferably comprises an indicator unit set up for indicating that the specified setting has been reached. The indicating unit preferably also indicates a sequence of coupling to the handheld drive unit. The indicator unit preferably indicates that the handheld drive unit is to be coupled to the corresponding interface. It is conceivable, for example, that the display unit comprises an LED light, and the LED light illuminates the first interface in a first color when the first interface is to be coupled to the handheld drive unit. After reaching the specified setting, the LED light then illuminates the first interface in a second color in order to indicate reaching the specified setting. The LED light then illuminates the second interface in the first color, in order to indicate the requesting of coupling the handheld drive unit to the second interface. The same applies for the other interfaces.

The manipulator preferably comprises one or more references for a surgical navigation system. In this manner, the manipulator can be integrated in a surgical navigation system and detected by the same.

According to a further preferred embodiment, markings are disposed at the interfaces for reading by a corresponding reading unit for determining a setting of the first and second joints. The markings are preferably disposed so that said markings are displaced when an actuating motion is transmitted from the handheld drive unit to the manipulator. Using said markings, the setting of the first and second suspension arm arrangements can be read and the setting of the first and second joints can thus be determined.

According to a further preferred embodiment, the manipulator is formed by means of a rapid prototyping method. The markings are preferably also applied by means of the rapid prototyping method. This is, on one hand, an inexpensive way for producing the manipulator, particularly if said manipulator is used as a single-use product. Said embodiment also has the advantage that the manipulator can be completely sterilized, as no electronics are provided in the manipulator. It is further also possible to adapt each manipulator to an individual patient in this manner. Parts of the kinematics of the manipulator can be smaller for children than for adults. In this case, planning software is preferable for the surgical intervention for automatically calculating and printing out the optimal kinematics from the anatomical structures and the planning data of the surgeon.

According to a further preferred embodiment, the manipulator is completely formed from a plastic material. PA12 or a comparable plastic is preferably used. By implementing the manipulator from plastic, said manipulator can be transparent to radiation, particularly X-ray radiation, and also usable in computed tomography or magnetic resonance imaging.

The field of application of the manipulator is thereby further expanded. Because the manipulator comprises no original drive, it is possible to implement the same for using in a magnetic resonance imaging system.

It is further preferable that the first suspension arm arrangement comprises a first and a second lever pivotably supported relative to each other and relative to the frame about pivot axes, and the pivot axes run parallel to each other, and the second suspension arm arrangement comprises a third and a fourth lever pivotably supported relative to each other and relative to the frame about pivot axes, and the pivot axes run parallel to each other and to the pivot axes of the first suspension arm arrangement. The installation space of the manipulator is thereby particularly reduced and a compact design is achieved.

The object indicated above is achieved in a second consideration of the invention by a handheld drive unit for using with a passive surgical manipulator according to any one of the preferred embodiments of a passive surgical manipulator described above, having a housing in which a drive motor is disposed in a control unit having a processor and software means, and an interface for temporarily and sequentially coupling to a corresponding interface of the manipulator and for transmitting an actuating motion to the manipulator, wherein the control unit is set up for controlling the drive motor such that an actuating motion is transmitted and is suitable for displacing the first and second joints and positioning the same in a predetermined specified position. It should be understood that the manipulator according to the first consideration of the invention and the drive unit according to the second consideration of the invention have identical and similar preferred refinements, as are particularly set forth in the dependent claims. In this respect, reference is made in full to the above description of the manipulator according to the first consideration of the invention.

The handheld drive unit can be of a similar type to a handheld grinder or a handheld electric toothbrush. Said drive unit is preferably substantially stick-shaped and preferably comprises the interface at one axial end for temporarily and sequentially coupling to the corresponding interface of the manipulator.

According to a first preferred embodiment of the drive unit, the interface of the drive unit comprises an output shaft. The output shaft preferably comprises an electronic contact for transmitting signals. In this manner, electronic signals can also be transmitted from the drive unit to the manipulator, or captured by the manipulator. For example, for the case that the manipulator comprises sensors for detecting forces or rotational orientations of individual elements, corresponding signals from said sensors can be transmitted to the drive unit via the interface.

It is further preferable that the output shaft comprises coupling means for coupling to the interfaces of the manipulator. Said coupling means can act in a form-fit or force-fit manner, particularly magnetically, as described above with reference to the manipulator.

It is thereby particularly preferable that the output shaft for each interface of the manipulator comprises a separate coupling means. This is particularly preferable if the interfaces of the manipulator are disposed in a common coupling cutout. A keying principle is particularly implemented here. For example, the output shaft in the drive unit comprises four axially offset gears or the like increasing in diameter from the tip toward the drive unit. The manipulator comprises corresponding discs having cutouts, so that the drive unit can be coupled to the manipulator in this manner.

According to a further preferred refinement, the control unit is implemented for receiving a predetermined specified position of the first and second joints. Said specified position is preferably provided by a surgical navigation system or the like. The control unit of the drive unit knows the kinematics of the manipulator and corresponding data is stored in the control unit of the drive unit to this end. Based thereon and based on the desired specified position and the current position of the manipulator, the required actuating motion is determined by the control unit of the drive unit.

The drive unit is then preferably implemented for determining the actuating motion required for reaching the specified position at each interface, based on the predetermined specified position of the first and second joints.

It is further preferable that the drive unit comprises a display panel, wherein the control unit is set up for indicating by means of the display panel that the specified setting has been reached. The drive unit transmits the actuating motion to the manipulator. That is, the drive of the drive unit stops moving when the specified position has been reached. It is nevertheless sensible to indicate that the specified position has been reached. Depending on the extent and speed of the motion, the duration of transmitting the motion to the manipulator varies in length and therefore it is preferable to inform the user that the specified position has been reached. The user can then remove the drive unit from the manipulator and place the drive unit at a further interface.

It is further preferable that the drive unit comprises a receptacle for a navigation tracker. A navigation system can thereby register that a user has introduced the drive unit into the surgical field and the surgical navigation system can cause one or more device to perform one or more actions, or to prevent such actions, based on that fact.

It is further preferable that the drive unit comprises at least one infrared radiation source, particularly an IR LED, for transmitting signals to a surgical navigation system. Such information can be particularly the reaching of the specified position, or also captured data of the manipulator, particularly such as forces at the joints. The drive unit can also transmit the specified position itself to the surgical navigation system, so that the surgical navigation system knows the position of the instrument in the surgical field. For this case, separately equipping the instrument with navigation trackers is not necessary.

According to a further embodiment of the drive unit, said unit comprises at least one sensor for determining a mechanical resistance acting at the interface, wherein the sensor is connected to the control unit and the control unit is set up for processing the captured data and/or for providing the same to a peripheral device. It can thereby be detected whether the instrument received at the manipulator contacts any resistance during the motion from the current position to the specified position, and whether the patient could thereby be injured. Safety is thereby further improved. It can be provided, for example, that the control unit and/or the peripheral device determines that a mechanical resistance exceeds a predetermined threshold value and that further transition of the manipulator into the specified setting is prevented.

The processing preferably comprises: determining forces acting on the first and second joints of the manipulator. In particular, forces acting at the tool center point are captured and determined.

According to a third consideration of the invention, the above object is achieved by a surgical system comprising at least one manipulator according to any one of the preferred embodiments of a passive surgical manipulator described above according to the first consideration of the invention and a drive unit according to any one of the preferred embodiments of a handheld drive unit described above according to the second consideration of the invention.

According to a fourth consideration of the invention, the above object is achieved by a method for setting a specified position of two joints of a passive surgical manipulator, particularly a manipulator according to the preferred embodiments of a passive surgical manipulator described above according to the first aspect of the invention, by means of a handheld drive unit, particularly a drive unit according to any one of the preferred embodiments of a handheld drive unit described above according to the second consideration of the invention, wherein the method comprises the steps: determining a current position of the two joints; determining a specified position of the two joints; determining actuating motions for the suspension arm arrangements of the manipulator, and transmitting the actuating motion by means of the handheld drive unit at interfaces of the manipulator provided for this purpose by temporarily and sequentially coupling the handheld drive unit to the corresponding interfaces of the manipulator. It should be understood that the manipulator according to the first consideration of the invention, the drive unit according to the second consideration of the invention, the system according to the third consideration of the invention, and the method according to the fourth consideration of the invention have identical and similar preferred refinements, as are particularly set forth in the dependent claims. In this respect, reference is made in full to the above description of the first, second, and third considerations of the invention.

For the method according to the fourth consideration of the invention, the transmitting of the actuating motion preferably comprises: coupling the handheld drive unit to a first interface of the manipulator; actuating the drive unit and transmitting a first actuating motion to the first interface for displacing a first supporting arm, particularly a lever, of the manipulator; decoupling the handheld drive unit from the first interface; coupling the handheld drive unit to a second interface of the manipulator; actuating the drive unit and transferring a second actuating motion to the second interface for displacing a second supporting arm, particularly a lever, of the manipulator; and decoupling the handheld drive unit from the second interface. The steps of transmitting the actuating motion are preferably performed in the sequence indicated.

BRIEF DESCRIPTION OF THE DRAWINGS

The invention is explained in more detail below using embodiment examples. Shown are.

DETAILED DESCRIPTION

Figure 1:
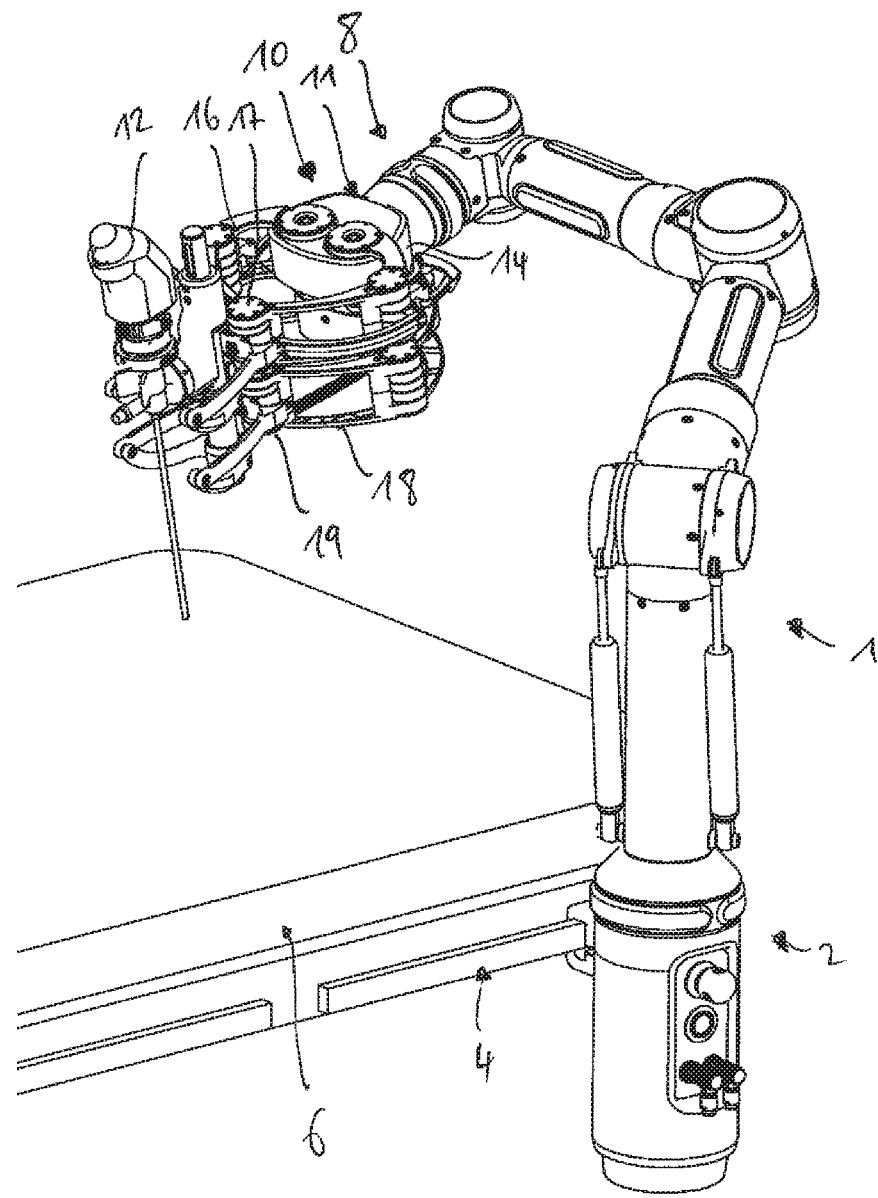
FIG. 1 a perspective view of a passive surgical manipulator attached to a robotic mounting arm.

FIG. 1 initially shows a robotic mounting arm 1 as is fundamentally known from DE 10 2014 016 842 A1, DE 10 2014 016 823 A1, and DE 10 2015 104 819 A1. The disclosed content thereof is fully incorporated herein. The mounting arm 1 comprises a proximal end 2 by means of which said arm is attached to a rail 4 of an operating table 6. A passive surgical manipulator 10 is received at the distal end 8 of the mounting arm 1. It should be understood that the passive surgical manipulator 10 can not only be received at the mounting arm 1 but also at other mounting systems, particularly such as stands or robots. The mounting arm 1 comprises a mounting segment 11 for attaching the manipulator 10. The manipulator 10 further supports a surgical instrument 12 implemented as an endoscope in the present embodiment example.

Figure 2:
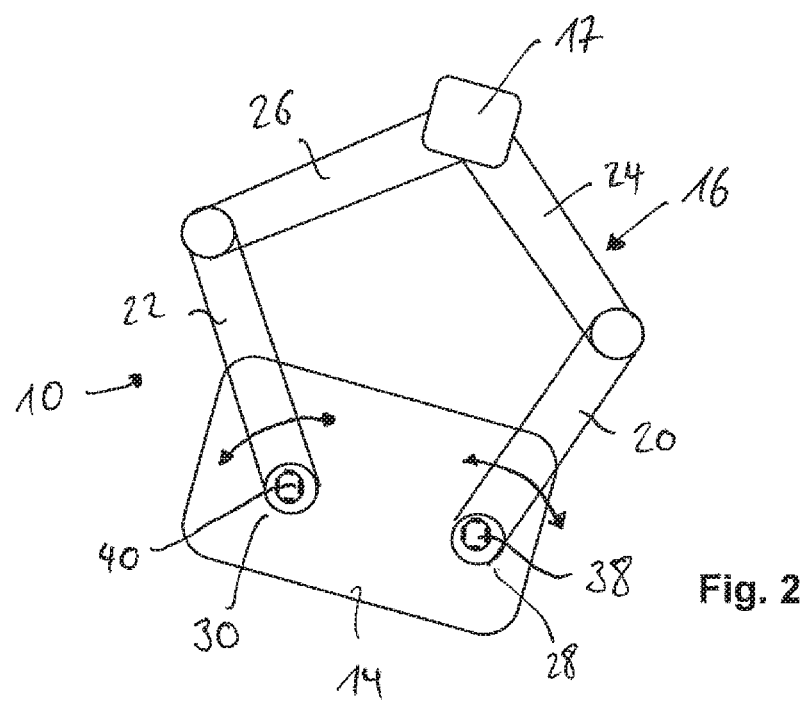
FIG. 2 a schematic plan view of the manipulator from FIG. 1.

The passive surgical manipulator 10 comprises a frame 14 (cf. FIG. 2) on which a first suspension arm arrangement 16 and a second suspension arm arrangement 18 (cf. FIG. 1) are disposed in an articulated manner. Only the first suspension arm arrangement 16 can be seen in FIG. 2, but the second suspension arm arrangement 18 is identical in design (cf. FIG. 1) and disposed behind the first suspension arm arrangement 16 with respect to the plane of the drawing in FIG. 2. The first suspension arm arrangement 16 comprises a first joint 17 and the second suspension arm arrangement comprises a second joint 19. The instrument 12 is received at the two joints 17, 19 (by means of a further mounting element in FIG. 1). By variously positioning the first and second joints 17, 19 accordingly, tipping of the instrument 12 is possible.

The statements about the first suspension arm arrangement 16 below should also apply to the second suspension arm arrangement 18, even if this is not explicitly stated.

The first suspension arm arrangement 16 comprises as a suspension arm a first lever 20 and a second lever 22 and a first bar 24 and a second bar 26. It should be understood that other configurations are also conceivable, as is explained later with reference to FIGS. 9 and 10.

It is also conceivable to apply the present invention to what is known as a four-bar linkage, wherein the four bars of the manipulator are disposed parallel and translationally displaceable relative to each other. The ends of the four bars are coupled to a transmission linkage having an instrument. By linearly displacing each bar accordingly, the instrument can be positioned. The bars thus form suspension arms in the sense of the invention. The same applies to three-bar linkages or linkages having five or more bars.

The first suspension arm arrangement 16 is connected to the frame 14 at first and second actuators 28, 30. The second suspension arm arrangement 28 is also connected to the frame 14 at third and fourth actuators 32, 34 (not visible in FIG. 2, cf. FIG. 5). The first and second levers 20, 22 and the third and fourth levers 24, 26 of the second suspension arm arrangement 18 (cf. FIG. 5) can be actuated by means of the actuators 28, 30, 32, 34, as indicated by the arrows in FIG. 2.

According to the invention, the first actuator 28 comprises a first interface 38, the second actuator comprises a second interface 40, the third actuator 32 comprises a third interface 42, and the fourth actuator 34 comprises a fourth interface 44. It is also possible, however, that further interfaces, particularly such as fifth, sixth, etc., are provided. This is particularly dependent on the linkage selected for the concrete embodiment.

Figure 3:
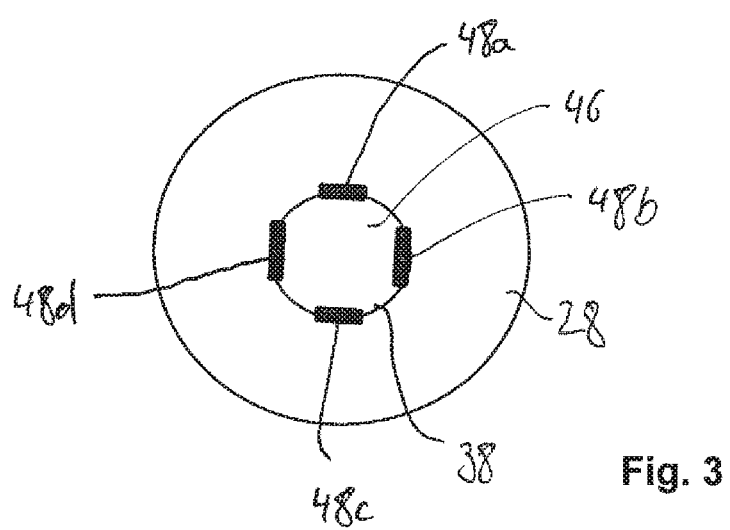
FIG. 3 a schematic detail view of an interface of the manipulator from FIG. 2.

FIG. 3 shows a magnified view of the actuator 38. The actuator 38 is implemented as a rotatable disc having an opening 46 comprising the interface 38. Electrical contacts 48*a*, 48*b*, 48*c*, 48*d* are disposed radially within the opening 46 for receiving and transmitting data. The lever 20 is then coupled to the actuator 38. The actuator 38 and the lever 20 can also be implemented as a single component, particularly non-removably without destroying said component.

Figure 4:
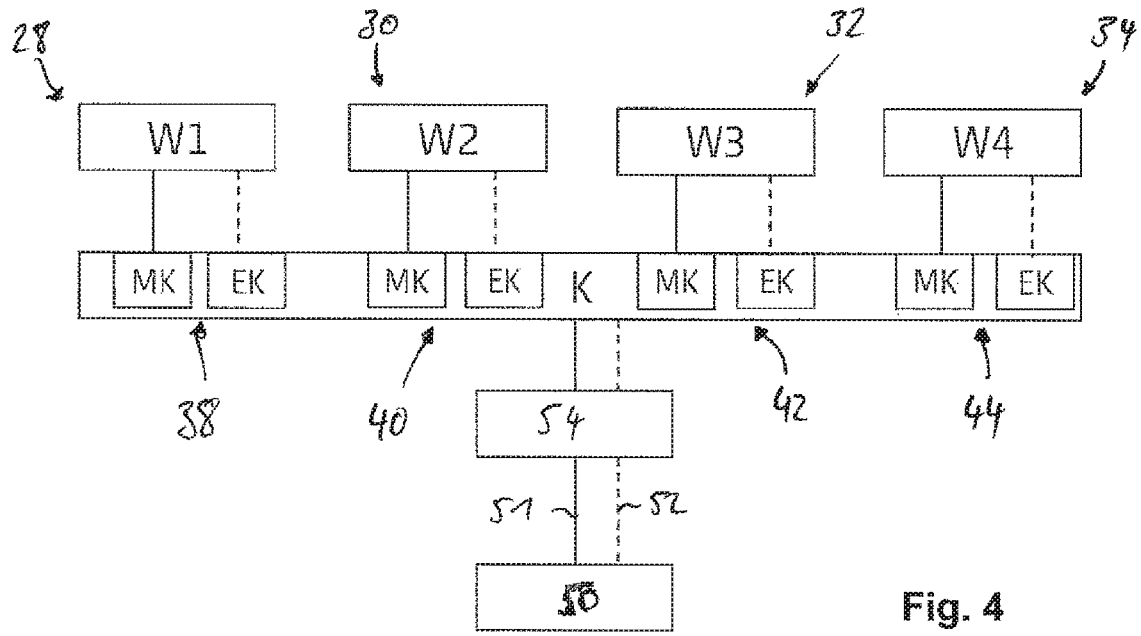
FIG. 4 a first variant of the arrangement of interfaces in a schematic view.
Figure 5:
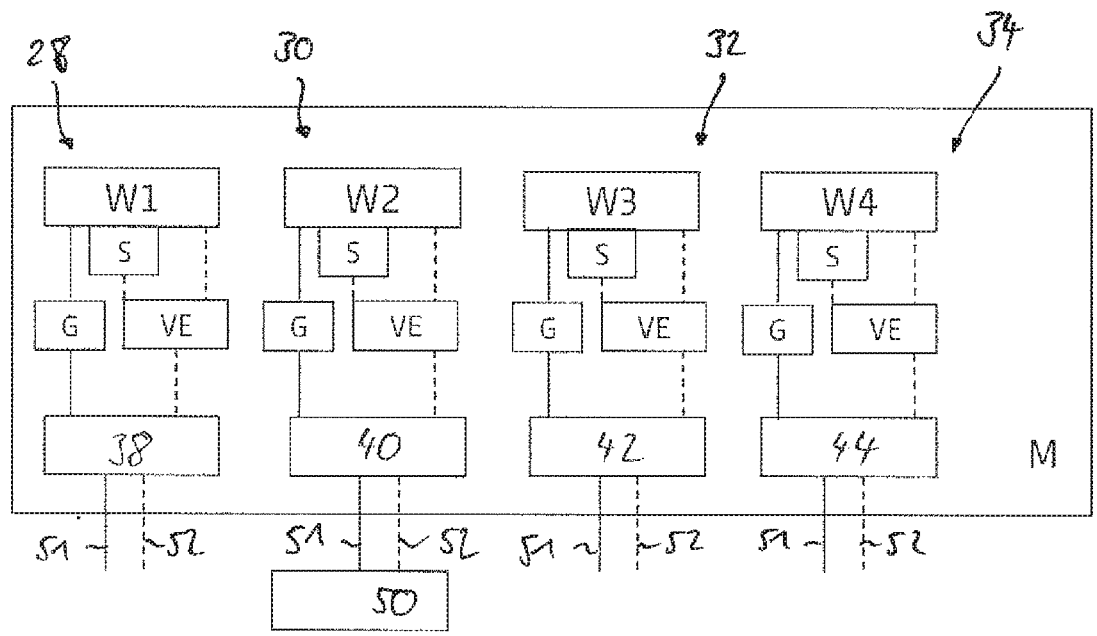
FIG. 5 a second variant of the arrangement of the interfaces in a schematic view.

FIGS. 4 and 5 illustrate two different embodiment examples of the interfaces 38, 40, 42, 44.

With reference initially to FIG. 4, a variant is described wherein the interfaces 38, 40, 42, 44 are not spatially separated from each other. In FIG. 4, said interfaces are indeed disposed adjacent to each other, but it should be understood that said interfaces are integrally disposed on a common coupling cutout 54. The handheld drive unit 50 need only be placed in the common coupling cutout 54 in this case, and contacts all four interfaces 38, 40, 42, 44 simultaneously. Said interfaces are separated within the common coupling cutout 54 and can be actuated separately. The separate interfaces 38, 40, 42, 44 each comprise a mechanical coupling MK and an electronic coupling EK having an integrated processing unit. In this respect, the coupling cutout 54 comprises a mechanical coupling 51 to the handheld drive unit 50 and an electrical connection 52 shown as a dashed line. In the same manner, the mechanical couplings MK are coupled via a mechanical coupling to corresponding drive shafts W1, W2, W3, W4 for the first, second, third, and fourth actuators 28, 30, 32, 34, and furthermore via an electrical line 52 to the electronic coupling EK.

For the second embodiment example of FIG. 5, the interfaces 38, 40, 42, 44 are spatially separated from each other. One interface 38, 40, 42, 44 is disposed in each axis of rotation of the levers 20, 22, 24, 26, that is, also in the axis of rotation of the actuators 28, 30, 32, 34. Each opening 46 of the interfaces 38, 40, 42, 44 is particularly disposed coaxial to the axis of rotation of the levers 20, 22, 24, 26. In the setting shown in FIG. 5, a handheld drive unit 50 is coupled to the second interface 40. The mechanical connection is indicated by means of the solid line 51 and the electrical connection by means of the dashed line 52. The interface 40 in turn is coupled to a corresponding drive shaft W2 for the second actuator 30 by means of a gear stage G and a processing unit VE. The processing unit VE is coupled to a sensor S by means of the electrical line, said sensor in turn measuring a force acting on the second shaft.

As can be seen from FIG. 5, each of the interfaces 38, 40, 42, 44 is equipped with corresponding lines 51, 52 and with corresponding gear stages G, processing units VE, sensors S, and shafts W1, W2, W3, and W4.

The embodiments of FIGS. 4 and 5 can also be combined. It is particularly conceivable to use the sensors of the variant according to FIG. 5 with the variant according to FIG. 4. It is further preferable that separate processing units VE according to FIG. 5 are used for the variant according to FIG. 4.

Figure 6:
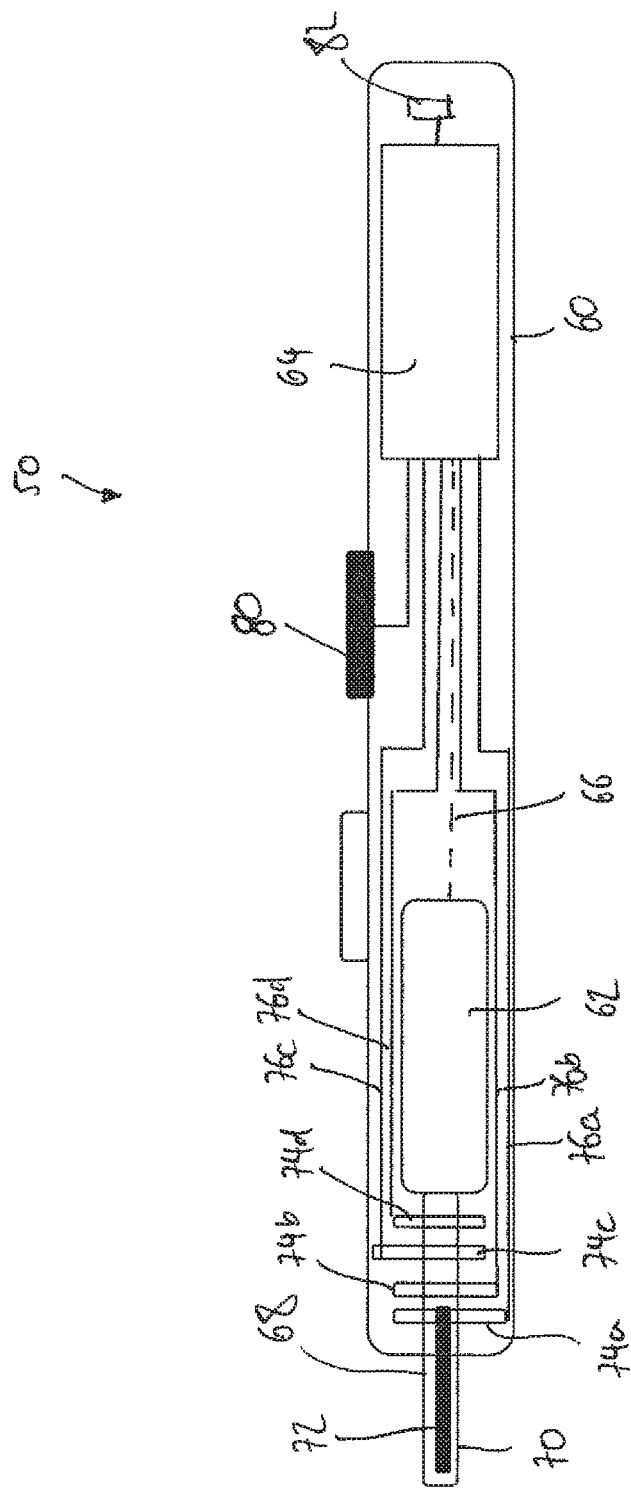
FIG. 6 a schematic section through a handheld drive unit according to a first embodiment example.

FIG. 6 illustrates a handheld drive unit 50 such as can be used with the embodiment according to FIG. 5. That is, the drive unit 50 according to FIG. 6 is provided for making contact with spatially separated interfaces 38, 40, 42, 44 and not with interfaces disposed within a common coupling cutout 54.

The handheld drive unit 50 comprises a housing 60, substantially stick-shaped in the present embodiment example, and resembling an electric toothbrush or handheld grinder in configuration. A drive motor 62 implemented as an electric motor is provided in the interior of the housing. The motor 62 is particularly implemented as an actuating motor. The motor 62 is connected to a control unit 64. The motor 62 receives electrical energy and actuating signals from the control unit 64 via a line 66 shown here as a dashed line, that is, particularly signals for a motion of the output shaft 68 thereof. The output shaft 68 of the drive unit 50 forms an interface 70 for temporarily and sequentially coupling to a corresponding interface 38, 40, 42, 44 of the manipulator and for transmitting an actuating motion to the manipulator 10. To this end, the output shaft 68 according to the present embodiment example comprises an electrical contact 72 for contacting the corresponding electrical contacts 48a, 48b, 48c, 48d connected to the processing unit VE or the electronic coupling EK. For accessing and transmitting data and signal to the electrical contact 72, four slip rings 74a, 74b, 74c, 74d are provided and in turn are coupled to the control unit 64 by means of signal lines 76a, 76b, 76c, 76d.

The output shaft 68 is implemented as fully magnetic in segments for coupling to the interfaces 38, 40, 42, 44 and the interfaces 38, 40, 42, 44 comprise corresponding, particularly ferromagnetic coupling elements, so that a rotational motion of the output shaft 68 can be transmitted by means of a force fit to the first and second suspension arm arrangements 16, 18.

The drive unit 50 finally comprises a display and operating panel 80 by means of which the drive unit 50 can be actuated.

The control unit 64 is implemented for receiving a predetermined specified position for the first and second joints 17, 19 by means of a wireless interface 82, and for determining an actuating motion required at each interface 38, 40, 42, 44 for reaching the specified position based on said received predetermined specified position. To this end, the configuration of the first and second suspension arm arrangements 16, 18 is saved in a memory unit in the control unit 64 and the control unit 64 determines by means of corresponding software means the required actuating motion at each interface 38, 40, 42, 44 based on the current position of the first and second joints 17, 19 and the specified position of the joints 17, 19. The required actuating motion in the present embodiment example is then embodied by a corresponding rotation of the output shaft 68 of the drive unit 50.

Figure 7:
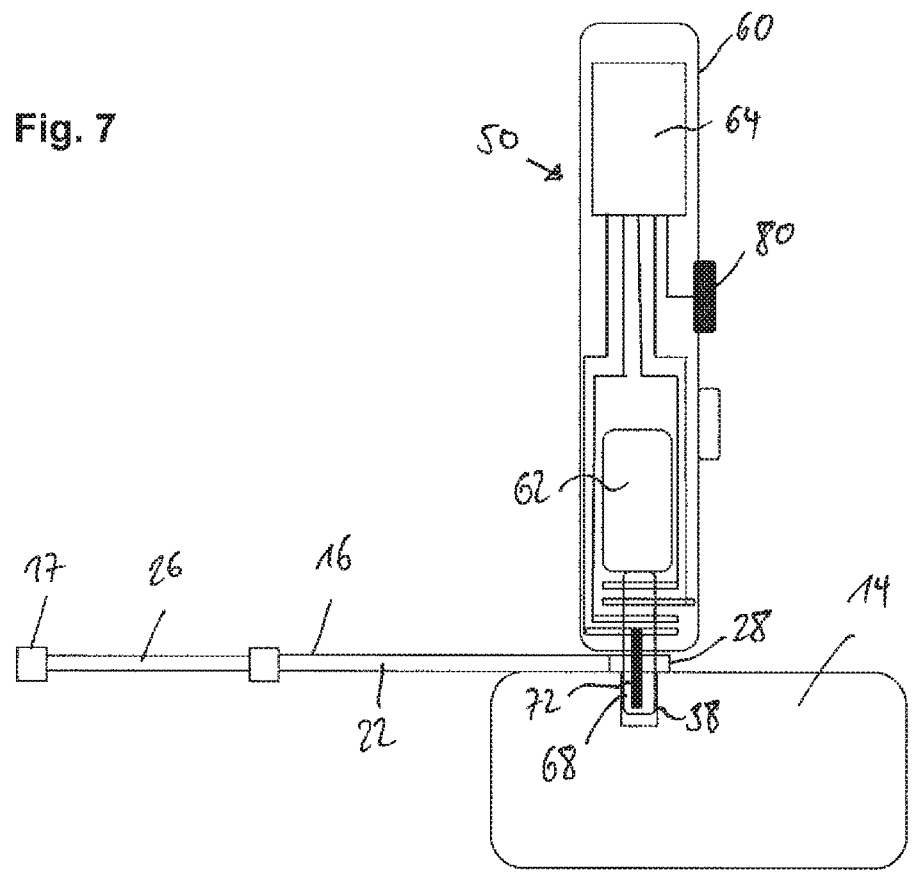
FIG. 7 the handheld drive unit according to FIG. 6 while coupled to an interface of the manipulator.

In the present embodiment example, the handheld drive unit 50 is initially coupled to an interface for transmitting the actuating motion, in the present embodiment example to the first interface 38 (FIG. 7). To this end, the output shaft 68 is inserted into the interface 38.

The fact that the user should perform said operation is indicated to the user by means of the display and operating panel 80. The display and operating panel 80 can indicate, for example, that the user should couple the drive unit 50 to the first interface 38. Once this is done, the control unit 64 actuates the motor 62 and the motor drives the output shaft 68 until the corresponding angle of rotation specified by the control unit 64 has been reached. The control unit 64 then switches off the drive 62. The first lever 22 is thereby pivoted and the joint 17 is displaced by means of the first bar 26.

Once the actuating motion has been transmitted to the first interface 38, a user can again decouple the drive unit 50 from the interface 38 and a corresponding signal is output on the display and operating panel 80. A further signal then appears on the display and operating panel 80, indicating to the user which of the interfaces 38, 40, 42, 44 the drive unit 50 should be coupled to next.

Figure 8:
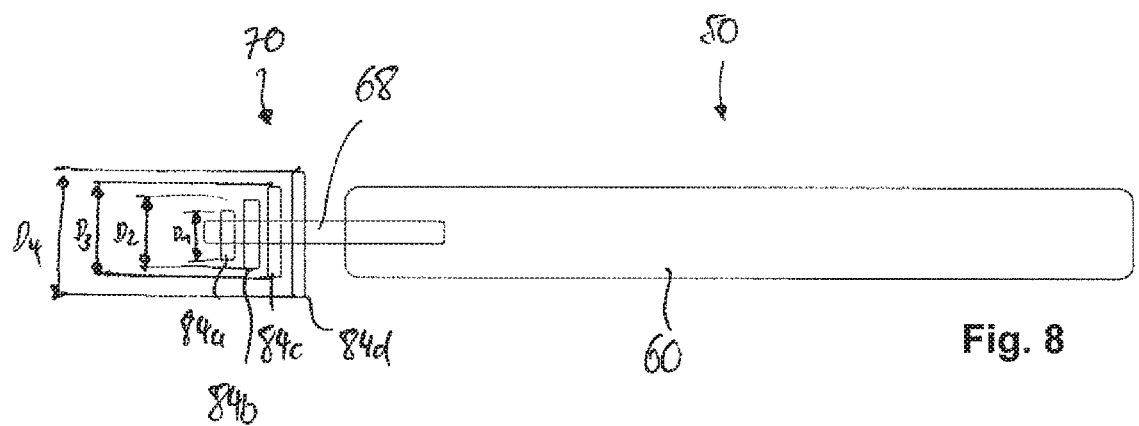
FIG. 8 a schematic side view of a second embodiment of the handheld drive unit.

In the variant described above from FIG. 4, wherein the interfaces 38, 40, 42, 44 are implemented in a common coupling cutout 54, the drive unit 50 is to be coupled only to said single coupling cutout 54. To this end, the drive unit 50 comprises an interface 70 provided particularly for this purpose, as shown in FIG. 8. The drive unit 50 according to the second embodiment example (FIG. 8) is implemented fundamentally identical to the drive unit 50 according to the first embodiment example (FIGS. 6, 7). The difference is substantially in the interface 70. The interface 70 is implemented for being able to simultaneously couple to all four interfaces 38, 40, 42, 44 disposed together in the common coupling cutout 54. To this end, four output discs 84a, 84b, 84c, 84d are disposed on the output shaft 68, the outer diameters D1, D2, D3, D4 thereof increasing from the distal end of the output shaft 68 to the proximal end, that is, toward the housing 60. Each of the output discs 84a, 84b, 84c, 84d can thus make contact with a corresponding coupling element of the first, second, third, and fourth interface 38, 40, 42, 44 and thus transmit the actuating motion. The individual output discs 84a, 84b, 84c, 84d can preferably be separately driven, for example by means of a plurality of hollow shafts nested one within the other in the output shaft 68. The output discs 84a, 84b, 84c, 84d can be implemented as gears, for example. Corresponding discs having central pass-through holes can be implemented in the coupling cutout 54, or separate coupling elements axially offset from the output shaft 68 and able to rotate about corresponding axes of rotation offset parallel to the output shaft 68.

Figure 9:
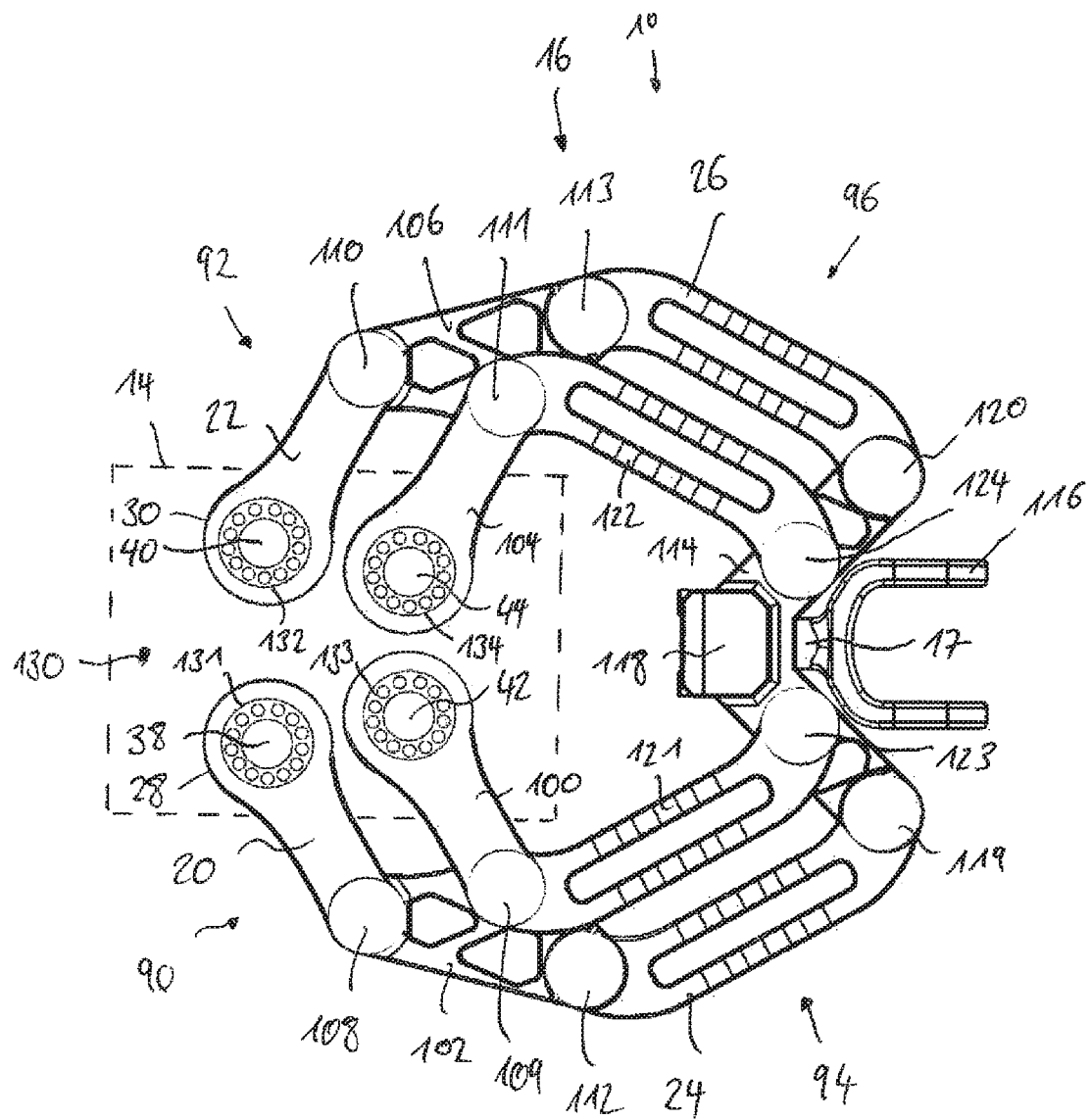
FIG. 9 a schematic plan view of a linkage of a manipulator according to a second embodiment example.

FIG. 9 illustrates a second embodiment example of the manipulator 10, wherein only the linkage of the manipulator 10, namely the first suspension arm arrangement 16, is shown in FIG. 9. Identical and similar elements are labeled with identical reference numerals, so that full reference is made to the above description.

The linkage of the suspension arm arrangement 16 is implemented as a double linkage in the present embodiment example (FIG. 9) and in this respect comprises a first, second, third, and fourth parallelogram 90, 92, 94, 96. The first parallelogram 90 is spanned by the first lever 20 and the second parallelogram 92 is spanned by the second lever 22. More precisely, the first parallelogram 90 is formed by the first lever 20, a fifth lever 100, a first suspension arm plate 102, and the frame 14 (shown only schematically in FIG. 9). The second parallelogram 92 is formed in a corresponding manner by the second lever 22, a sixth lever 104, a second suspension arm plate 106, and the frame 14. The suspension arms 20, 22, 100, 104 are connected to the corresponding suspension arm plate 102, 106 in an articulated manner by means of joints 108, 109, 110, 111.

The first and second bars 24, 26 are then connected to the suspension arm plates 102, 106 and in turn are connected to the corresponding suspension arm plate 102, 106 by means of joints 112, 113. At the other end, the first and second bars 24, 26 are connected by means of a bracket 114 forming the joint 17 for the instrument. A further U-bracket 116 is disposed above the joint 17 in the present embodiment example for receiving the instrument. More precisely, the U-bracket 116 is coupled to a linear drive 118 for linearly displacing the U-bracket 116 in the plane of the drawing with respect to FIG. 9.

The first and second bars 24, 26 are connected to the bracket 114 by means of joints 119, 120. Fifth and sixth bars 121, 122 are provided for spanning the third and fourth parallelograms 94, 96 and are connected at one side to the suspension arm plates 102, 106 at the joints 109, 11 and at the other end to the bracket 114 by means of joints 123, 124. The present particular arrangement of the parallelograms 90, 92, 94, 96 achieves particular stability. Adjusting two of the levers, particularly the first and second levers 20, 22, is sufficient for displacing the first joint 17. The fifth and sixth levers 100, 104 can travel along passively.

In this respect, the first and second levers 20, 22, as was described with reference to the preceding embodiment examples, are coupled to first and second actuators 28, 30 comprising the first and second interfaces 38, 40. That is, the handheld drive unit 50 according to the first embodiment example (FIG. 6) can be coupled to the first interface 38 and/or to the second interface 40 for adjusting the first suspension arm arrangement according to the present embodiment example (FIG. 9) in order to drive the first and second levers 20, 22 while the fifth and sixth levers 100, 104 travel along passively.

It can be seen in FIG. 9 that the third and fourth interfaces 42, 44 are implemented at the fifth and sixth levers 100, 104. The levers 100, 104 are not driven by means of the third and fourth interfaces 42, 44, however, but rather the levers of the second suspension arm arrangement 18 not shown in FIG. 9. The second suspension arm arrangement 18 is below the first suspension arm arrangement 16 with respect to the plane of the drawing in FIG. 9, and is implemented identically. For the second suspension arm arrangement 18, however, the levers 20, 22 on the left with respect to FIG. 9 are not driven, but rather the corresponding levers disposed parallel to and below the fifth, sixth levers 104. In this manner, both the first and the second suspension arm arrangement 16, 18 can be operated from one side of the manipulator 10, while for the first embodiment example, as shown in FIG. 1, the drive unit is first coupled to the first suspension arm arrangement 16 from above and then to the second suspension arm arrangement 18 from below. Operating is thereby further simplified.

A further feature visible in FIG. 9 is an indicator device 130. The indicator device 130 comprises four LED rings 131, 132, 133, 134 disposed coaxially about the axes of rotation of the levers 20, 22, 100, 104 and about the interfaces 38, 40, 42, 44 in the present embodiment. Said LED rings 131, 132, 133, 134 indicate to a user at which of the interfaces 38, 40, 42, 44 the user should apply the handheld drive unit 50 in order to adjust the pose of the first and second suspension arm arrangement 16, 18 and thus the position of the joints 17, 19. It can also be provided that before and/or during the transmitting of the actuating motion the LED rings 131, 132, 133, 134 take on a different color, or the individual LED elements of the LED rings 131, 132, 133, 134 are illuminated in a rotary manner in order to indicate the direction of rotation of the levers 20, 22, 100, 104. It can also be provided that the LED rings 131, 132, 133, 134 indicate that the specified position has been reached by lighting up in a further color, by flashing, or by otherwise lighting up.

It is also possible that the reaching and/or exceeding of a predetermined threshold value with respect to a force acting on the joints 17, 19 or a tool center point is indicated by means of the LED rings 131, 132, 133, 134. To this end, the LED rings 131, 132, 133, 134 are preferably connected to the processing units VE (cf. FIG. 5).

Figure 10:
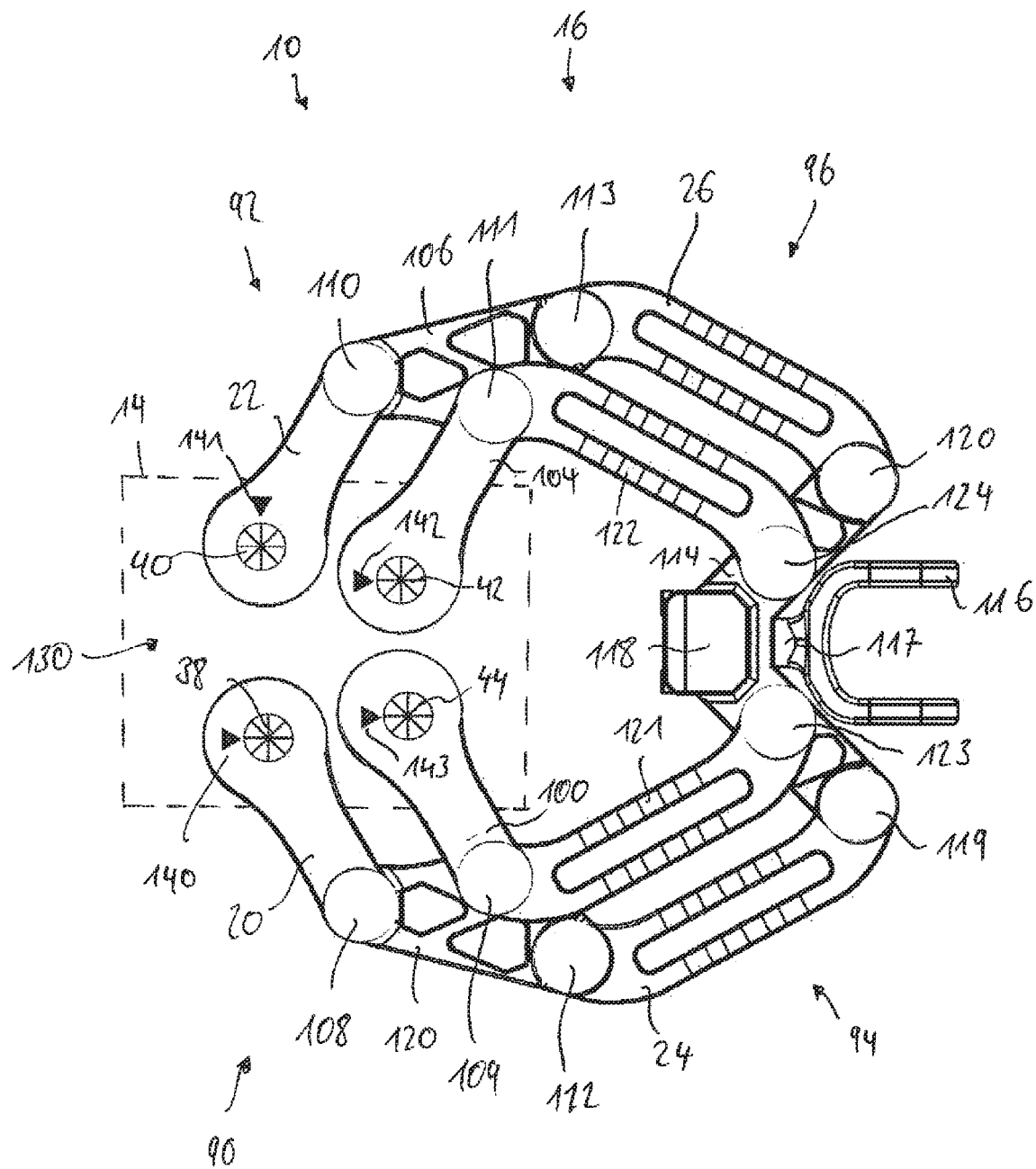
FIG. 10 a schematic plan view of a manipulator according to a third embodiment example.

FIG. 10 illustrates a third embodiment example of the manipulator 10, and particularly a third embodiment example of the first suspension arm arrangement 16. Identical and similar elements are again labeled with identical reference numerals and in this respect, full reference is made to the above description. The linkage of the suspension arm arrangement 16 according to the present embodiment example (FIG. 10) is particularly identical in design to the linkage of the suspension arm arrangement 16 of the second embodiment example (FIG. 9). In this respect, the differences between the embodiment examples according to FIGS. 9 and 10 are particularly explained below.

The substantial difference between the two present embodiment examples is the indicator device 130. While said device comprises four LED rings 131, 132, 133, 134 in the embodiment example according to FIG. 9, a purely mechanical indicator device 130 is provided in the embodiment example in FIG. 10. The manipulator 10 according to the embodiment example from FIG. 10 comprises no electronic components whatsoever and is thus suitable for use in a computed tomography system. The mechanical indicator device 130 comprises markings 140, 141, 142, 143 coupled to the corresponding interfaces 38, 40, 42, 44. The markings 140, 141, 142, 143 indicate a rotational orientation of the corresponding lever and are visually detectable.

Figure 11:
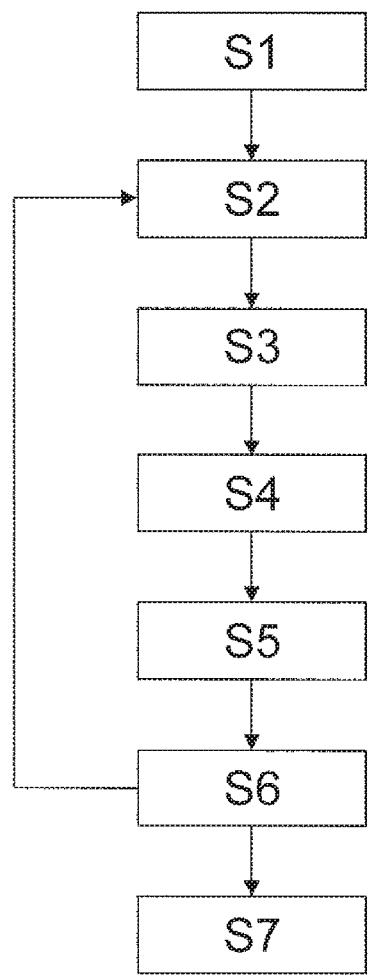
FIG. 11 a schematic representation of a method according to the invention.

According to FIG. 11, finally, an embodiment example is shown for a method for setting a specified position of two joints 17, 19 of a passive surgical manipulator 10 according to any one of the embodiments described above.

The method shown in FIG. 11 particularly relates to the second embodiment example according to FIG. 9. It should be understood, however, that an indicator device 130 as is shown in the second embodiment example according to FIG. 9 can also be provided in the first embodiment example according to FIGS. 1 through 8. For the embodiment example according to FIG. 1, the LED rings 131, 132, 133, 134 would then be disposed on correspondingly opposite sides of the frame 14.

In the method shown in FIG. 11, a specified pose has already been received at a control unit of the manipulator 10 or an external control unit. In step S1, calculating the target pose of the first and second suspension arm arrangements 16, 18 and the sequential motion sequence and profiles of the individual degrees of freedom of the suspension arm arrangement 16, 18 takes place. That is, a calculation is made as to how the individual levers 20, 22, 100, 104 should be rotated in order to bring the joints 17, 19 to the desired position.

In step S2, a first LED ring 131 is lit up deviating from the other LED rings 132, 133, 134 in order to indicate that the drive unit 50 is to be coupled to the interface 38 associated with said LED ring 131. To this end, a corresponding signal is sent from the control unit to the corresponding LED ring 131.

In step S3, a user couples the handheld drive unit 50 to the interface 38 indicated by the LED ring 131. The handheld drive unit 50 registers the coupling and then transmits the predetermined actuating motion to the correspondingly associated first suspension arm arrangement 16 by means of the interface 38. It can also be provided that the handheld drive unit 50 does not automatically register the coupling to the first interface. In this case, a user uses the display and operating panel 80 of the handheld drive unit 50 to enable the same in order to transmit the actuating motion to the interface 38. To this end, a menu can be displayed on the display and operating panel.

By switching on the rotor 62 of the handheld drive unit 50, the actuating motion is transmitted in step 4 for a long enough time that the desired specified position of the corresponding degree of freedom has been reached.

In step 5, after reaching said position, the motor 62 is switched off by the control unit 64 of the handheld drive unit 50 and the LED ring 131 of the corresponding interface 38 changes color to indicate that the specified position has been reached.

In step S6, a decision is then made as to whether a further degree of freedom is to be adjusted. For this case, as the arrow leading to step 2 indicates, a further LED ring, such as LED ring 132, lights up in order to indicate coupling the handheld drive unit 50 to the correspondingly associated interface 40. Steps S2, S3, S4, and S5 then follow in an analogous manner with respect to each interface 38, 40, 42, 44. If it is determined in step 6 that no further adjusting is required, then in step 7 it is determined that adjusting is completed. This can be indicated by simply lighting up all of the LED rings 131, 132, 133, 134, or by another type of indicating, such as changing the color of the LED rings, for example, or by means of an acoustic signal, and/or by means of the display and operating panel 80.

The invention claimed is:

1. A passive surgical manipulator for holding and positioning a surgical instrument, the manipulator comprising:
a frame;
a first suspension arm arrangement comprising at least one suspension arm and connecting the frame to a first joint associated with the instrument in an articulated manner; and
a second suspension arm arrangement comprising at least one suspension arm and connecting the frame to a second joint associated with the instrument in an articulated manner,
wherein the first joint is displaceable in a first motion plane and the second joint is displaceable in a second motion plane,
wherein the first suspension arm arrangement is connected to the frame at first and second actuating devices and the second suspension arm arrangement is connected to the frame at third and fourth actuating devices,
wherein the first actuating device comprises a first interface, the second actuating device comprises a second interface, the third actuating device comprises a third interface, and the fourth actuating device comprises a fourth interface for temporarily receiving a corresponding interface of a handheld drive unit,
wherein the handheld drive unit is configured to be coupled temporarily and sequentially to the first, second, third, and fourth interfaces for transferring an actuating motion in order to displace the first and second joints to a predetermined, specified position.

2. The manipulator according to claim 1, wherein the first and second suspension arm arrangements are configured to be self-blocking.

3. The manipulator according to claim 1, further comprising a mounting segment for mounting the manipulator on a surgical mounting arm.

4. The manipulator according to claim 1, wherein the first, second, third, and fourth interfaces are spatially separated from each other.

5. The manipulator according to claim 1, wherein the first, second, third, and fourth interfaces are implemented for positively receiving the handheld drive unit and for positively transmitting the actuating motion.

6. The manipulator according to claim 1, further comprising at least one sensor for determining the force acting on the first and/or the second joint.

7. The manipulator according to claim 1, further comprising a control unit having a processor form for determining an actuating motion required at each interface for reaching a specified setting based on a predetermined specified setting for the first and second joints.

8. The manipulator according to claim 7, wherein the control unit is configured to provide signals representing the determined actuating motions at the handheld drive unit or a peripheral device.

9. The manipulator according to claim 7, wherein each interface comprises an indicator for indicating that the specified setting has been reached.

10. The manipulator according to claim 9, wherein the indicator is configured to indicate a sequence of coupling to the handheld drive unit.

11. The manipulator according to claim 1, further comprising markings readable by a corresponding reading unit disposed at the first, second, third, and fourth interfaces for determining a setting of the first and second joints.

12. The manipulator according to claim 1, wherein:
the first suspension arm arrangement comprises a first lever and a second lever pivotably supported relative to each other and relative to the frame about pivot axes, and the pivot axes run parallel to each other, and
the second suspension arm arrangement comprises a third lever and a fourth lever pivotably supported relative to each other and relative to the frame about pivot axes, and the pivot axes run parallel to each other and to the pivot axes of the first suspension arm arrangement.

13. A hand-held drive unit for use with the passive surgical manipulator according to claim 1, the drive unit comprising:
a housing in which a drive motor and a control unit having a processor disposed; and
an interface for temporarily and sequentially coupling to a corresponding interface of the manipulator and for transmitting an actuating motion to the manipulator,
wherein the control unit is configured to control the drive motor such that an actuating motion is transmitted for displacing the first and second joints in a predetermined specified position.

14. The drive unit according to claim 13, wherein the interface comprises an output shaft.

15. The drive unit according to claim 14, wherein the output shaft comprises coupling means for coupling to the first, second, third, and fourth interfaces of the manipulator.

16. The drive unit according to claim 13, further comprising a display panel, wherein the control unit is configured to indicate that a specified setting has been reached via the display panel.

17. The drive unit according to claim 16, wherein the control unit is configured to indicate one or more system statuses of the drive unit and/or of the manipulator via the display panel.

18. The drive unit according to claim 13, further comprising at least one infrared radiation source for transmitting signals to a surgical navigation system.

19. The drive unit according to claim 13, further comprising at least one sensor for determining a mechanical resistance acting at the interface, wherein the sensor is connected to the control unit and the control unit is configured to determine forces acting on the first and second joints of the manipulator based on data from the sensor and to provide the determined forces to a peripheral device.

20. The drive unit according to claim 13, further comprising a warning device connected to the control unit, wherein the control unit is configured to output a warning signal by means of the warning device when the control unit determines a critical situation.

21. A method for setting a specified position of the first and second joints of the passive surgical manipulator of claim 1, the method comprising:
determining a current position of the first and second joints;
determining a specified position of the first and second joints;
determining actuating motions for each suspension arm arrangement of the manipulator; and
transferring the actuating motion via the handheld drive unit at the first, second, third, and fourth interfaces of the manipulator by temporarily and sequentially coupling the handheld drive unit to the corresponding interfaces of the manipulator.

22. The method according to claim 21, wherein transferring of the actuating motion comprises:
coupling the handheld drive unit to the first interface of the manipulator;
actuating the drive unit and transferring a first actuating motion to the first interface for displacing a first supporting arm of the manipulator;
decoupling the handheld drive unit from the first interface;
coupling the handheld drive unit to the second interface of the manipulator;
actuating the drive unit and transferring a second actuating motion to the second interface for displacing a second supporting arm of the manipulator; and
decoupling the handheld drive unit from the second interface.

* * * * *